United States Patent
Mishima et al.

(10) Patent No.: US 7,500,969 B2
(45) Date of Patent: *Mar. 10, 2009

(54) DISPOSABLE DIAPER

(75) Inventors: Yoshitaka Mishima, Mitoyo-gun (JP); Kaiyo Nakajima, Mitoyo-gun (JP)

(73) Assignee: Uni-Charm Corporation, Ehime-Ken (JP)

( * ) Notice: Subject to any disclaimer, the term of this patent is extended or adjusted under 35 U.S.C. 154(b) by 379 days.

This patent is subject to a terminal disclaimer.

(21) Appl. No.: 11/105,558

(22) Filed: Apr. 14, 2005

(65) Prior Publication Data
US 2005/0234421 A1    Oct. 20, 2005

(30) Foreign Application Priority Data
Apr. 14, 2004    (JP) ............................. 2004-118895

(51) Int. Cl.
*A61F 13/15*    (2006.01)

(52) U.S. Cl. .................... 604/385.201; 604/385.19; 604/385.01; 604/396; 604/398; 604/385.3

(58) Field of Classification Search .......... 604/385.201, 604/385.19, 385.01, 396, 398, 385.3
See application file for complete search history.

(56) References Cited

U.S. PATENT DOCUMENTS

| | | |
|---|---|---|
| 3,211,147 A | 10/1965 | Pherson et al. |
| 3,650,273 A | 3/1972 | Schaar |
| 3,653,382 A | 4/1972 | Easley et al. |
| 3,776,233 A | 12/1973 | Schaar |
| 3,816,227 A | 6/1974 | Schaar |
| 3,848,599 A | 11/1974 | Schaar |
| 3,885,568 A | 5/1975 | Scharr |
| 3,943,930 A | 3/1976 | Schaar |
| 4,573,990 A | 3/1986 | Ohsaki |
| 4,695,278 A | 9/1987 | Lawson |
| 4,944,735 A | 7/1990 | Mokry |
| 5,514,121 A | 5/1996 | Roe et al. |
| 5,954,705 A | 9/1999 | Sawaki et al. |
| 6,869,423 B2 | 3/2005 | Onishi et al. |
| 2002/0007171 A1 | 1/2002 | Takei et al. |
| 2002/0045872 A1 | 4/2002 | Shimada et al. |
| 2002/0111594 A1* | 8/2002 | Onishi et al. ................. 604/379 |

FOREIGN PATENT DOCUMENTS

EP            955028 A2       11/1999

(Continued)

OTHER PUBLICATIONS

EP Search Report issued Aug. 13, 2007 for EP 05 72 8449.

*Primary Examiner*—Jacqueline F. Stephens
(74) *Attorney, Agent, or Firm*—Lowe Hauptman Ham & Berner, LLP

(57) ABSTRACT

A disposable diaper is formed in a crotch region with a body fluid absorbent panel extending in a back-and-forth direction of the diaper and in the vicinity of transversely opposite side edges of the crotch region with elastic leak-barrier cuffs extending in the back-and-forth direction. The leak-barrier cuffs are normally under a tension in the back-and-forth direction. The body fluid absorbent panel is formed with first folding guide means extending across the body fluid absorbent panel, along which the body fluid absorbent panel can be folded to bring the body fluid absorbent panel close to the diaper wearer.

5 Claims, 6 Drawing Sheets

FOREIGN PATENT DOCUMENTS

| | | |
|---|---|---|
| EP | 1 216 678 A3 | 6/2002 |
| EP | 1 234 563 A3 | 8/2002 |
| FR | 2 546 745 | 12/1984 |
| GB | 2 283 663 A3 | 5/1995 |
| JP | 2002-315778 | 10/2002 |
| JP | 2003-079664 | 3/2003 |

* cited by examiner

DISPOSABLE DIAPER

RELATED APPLICATIONS

The present application is based on, and claims priority from, Japanese Application Number 2004-118895, filed Apr. 14, 2004, the disclosure of which is hereby incorporated by reference herein in its entirety.

BACKGROUND OF THE INVENTION

This invention relates to a disposable diaper and more particularly to a disposable diaper adapted to block a undesirable movement of urine and loose passage possibly occurring in a back-and-forth direction.

There has already been proposed disposable diapers free from an anxiety that urine and loose passage might commingle together in a crotch region of the diaper and consequentially soil the wearer's skin in the crotch region. For example, a disposable diaper disclosed in Japanese Unexamined Patent Application Publication No. 2002-315778 (Reference) is an example of such a diaper. In this known diaper, a relatively large comprising a body fluid absorbent first core is sandwiched between a liquid-pervious sheet and a liquid-impervious sheet extends over a rear waist region and a crotch region. This diaper further includes a relatively small panel comprising a second body fluid absorbent core covered with a liquid-pervious sheet so as to extend over the front waist region and a part of the crotch region. In the crotch region, the relatively large panel overlaps the relatively small panel lying on the side of the inner surface of the diaper to form between these two panels a pocket opening toward the rear waist region. Loose passage moving forward from the rear waist region is guided into this pocket and unable to move forward beyond this pocket. In this way, this diaper can solve the problem that urine and loose passage might commingle together in the crotch region and soil the wearer's skin.

In the diaper disclosed in Reference, the body fluid absorbent panel comprises a pair of panels, i.e., the relatively large panel and the relatively small panel. Correspondingly, the diaper disclosed in Reference has a construction more complicated and costly than the conventional disposable diapers. In addition, these two panels overlapping each other in the crotch region inevitably make the crotch region bulky and may create a feeling of discomfort against the wearer.

SUMMARY OF THE INVENTION

An object of this invention is to provide a disposable diaper adapted to solve, with a simplified construction, such a problem encountered when it is attempted to prevent urine and loose passage from commingling together.

According to this invention, there is provided a disposable diaper having a back-and-forth direction and a transverse direction being orthogonal to the back-and-forth direction, the diaper comprising: a front waist region, a rear waist region, a crotch region extending between the front and rear waist regions, a body fluid absorbent panel provided in at least said crotch region of the regions and extending in the back-and-forth direction, and leak-barrier cuffs lying in a vicinity of side edges of the body fluid absorbent panel being opposite to each other in the transverse direction and extending in the back-and-forth direction, the leak-barrier cuffs respectively having proximal edges and distal edges in the transverse direction, wherein the distal edges are bonded to the body fluid absorbent panel in the vicinity of the respective side edges thereof while the distal edges are laid inside with respect to the respective proximal edges and elastically stretch- and contractable in the back-and-forth direction so as to cover a part of the body fluid absorbent panel.

The diaper according to this invention further comprises the body fluid absorbent panel in the crotch region being formed with first folding guide means extending across the body fluid absorbent panel in the transverse direction so that the body fluid absorbent panel is folded inward along the first folding guide means to describe a generally inverted V-sectional shape.

In the case of the disposable diaper according to this invention, the leak-barrier cuffs contract as the diaper is put on the wearer and bows inward. The contraction of the leak-barrier cuffs affects the body fluid absorbent panel to have its dimension in the back-and-forth direction reduced. Thereupon the body fluid absorbent panel is folded inward along the first folding guide means to form the crest describing the generally inverted V-sectional shape and rising toward the wearer in a vicinity of the first folding guide means. This crest functions to prevent urine from moving rearward and, at the same time, to prevent loose passage from moving forward. Thus it is possible for this disposable diaper to prevent urine and loose passage from commingling together in the crotch region with the absorbent panel.

According to one preferred embodiment of this invention, the body fluid absorbent panel is formed with, in addition to the first folding guide means, second folding guide means lying aside from the first folding guide means toward the front waist region and extending in parallel to the first folding guide means along which the body fluid absorbent panel can be folded so as to describe a generally V-sectional shape and third folding guide means lying aside from the first folding guide means toward the rear waist region and extending in parallel to the first folding guide means along which the body fluid absorbent panel can be folded so as to describe a generally V-sectional shape or at least the folding guide means.

With the disposable diaper of such an arrangement, the body fluid absorbent panel is folded along the second and third folding guide means to form the trough which facilitates the crest to be formed. Therefore, the crest is more reliably formed in a vicinity of the first folding guide means so far as the body fluid absorbent panel has at least one of these second and third folding guide means.

According to another preferred embodiment of this invention, the distal edges of respective the leak-barrier cuffs are bonded to the body fluid absorbent panel in the vicinity of the first folding guide means.

With the disposable diaper of such an arrangement, the crest is further more reliably formed in the vicinity of the first folding guide means because the distal edges of the respective leak-barrier cuffs function to draw up the body fluid absorbent panel in the vicinity of the first folding guide means as these distal edges of the leak-barrier cuffs contract.

According to still another preferred embodiment of this invention, the body fluid absorbent panel comprises a liquid-pervious upper sheet destined to come in contact with the wearer, a liquid-impervious or liquid-pervious lower sheet and a body fluid absorbent core interposed between these two sheets and wherein the first folding guide means is a generally inverted V-shaped groove extending on the side of the lower sheet of the body fluid absorbent panel in the transverse direction and the second and third folding guide means are generally V-shaped grooves extending on the side of the upper sheet of the body fluid absorbent panel in the transverse direction.

In the disposable diaper according to this embodiment of the invention, the body fluid absorbent panel has, in addition to the first folding guide means in the form of the generally inverted V-shaped groove, the second and third folding guide means in the form of the generally V-shape grooves so that the body fluid absorbent panel can easily form the crest in the vicinity of the first folding guide means and easily form the trough in the vicinity of the second and third folding guide means as the leak-barrier cuffs bow in the back-and-forth direction.

DETAILED DESCRIPTION OF THE PREFERRED EMBODIMENTS

Details of a disposable diaper according to this invention will be more fully understood from the description given hereunder with reference to the accompanying drawings.

Figure 1:
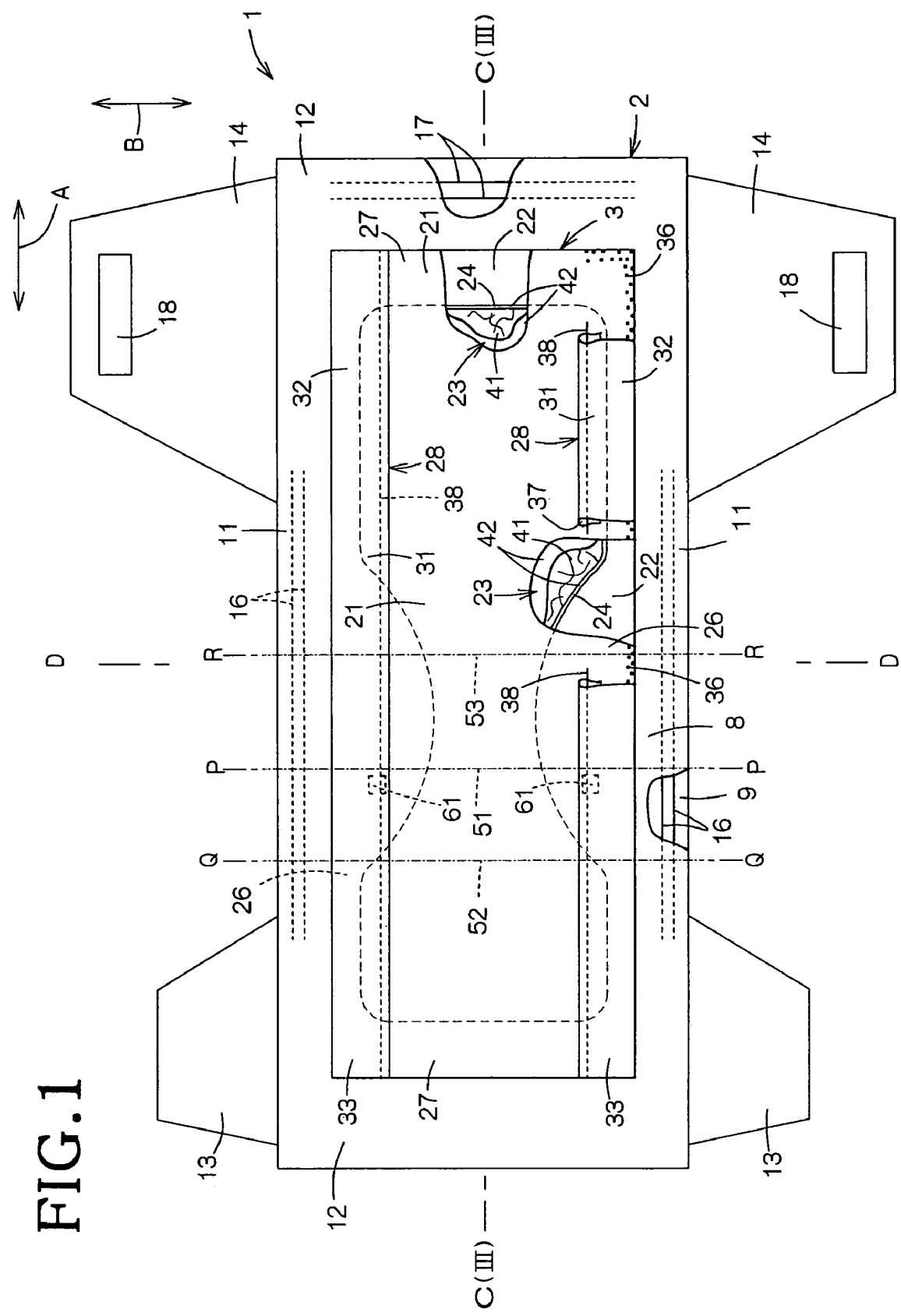
FIG. 1 is a partially cutaway plan view showing a disposable diaper as a first embodiment of the invention.
Figure 2:
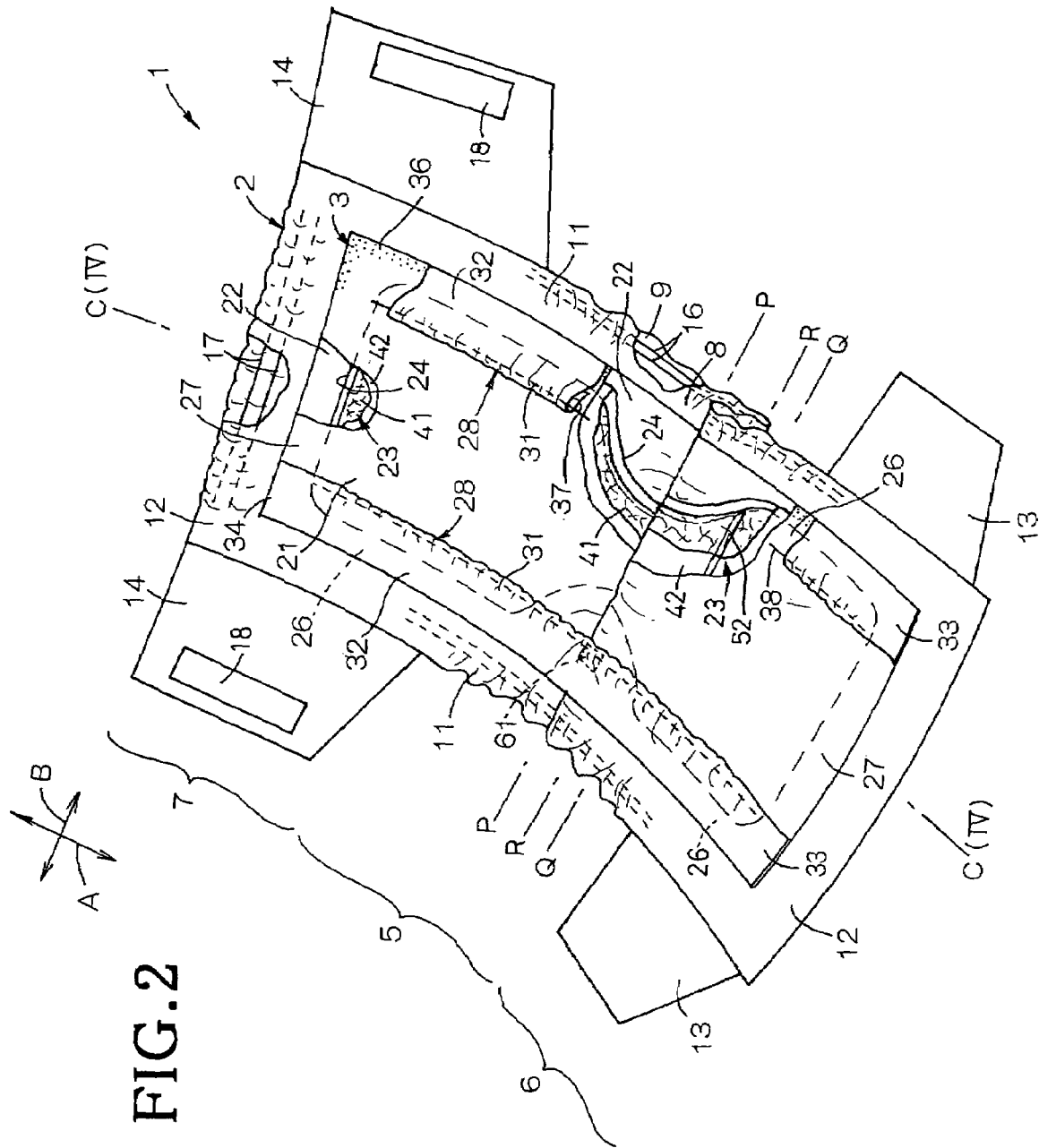
FIG. 2 is a partially cutaway perspective view showing the disposable diaper as left bow.

FIG. 1 is a partially cutaway plan view showing a disposable diaper 1 as a first embodiment of the invention and FIG. 2 is a partially cutaway perspective view showing the diaper 1 as left bow under the contraction of elastic members which will be described later. The diaper 1 has a back-and-forth direction indicated by a double-headed arrow A and a transverse direction indicated by a double-headed arrow B orthogonal to the arrow A. Basically, the diaper 1 comprises a chassis 2 shaped in a rectangle which is relatively long in the back-and-forth direction A and a body fluid absorbent panel 3 attached to the chassis 2. The chassis 2 comprises a topsheet 8 made of liquid-impervious plastic film and a backsheet 9 made of nonwoven fabric bonded to the inner surface of the topsheet 8. The chassis 2 is contoured by a pair of side edges 11 extending in the back-and-forth direction A and a pair of ends 12 extending in the transverse direction B. As for the configuration, the chassis 2 defines in the back-and-forth direction A, a crotch region 5, a front waist region 6 extending forward from the crotch region 5 and a rear waist region 7 extending rearward from the crotch region 5. A pair of front wings 13 extend in the transverse direction B from the respective side edges 11 of the front waist region 6 and a pair of rear wings 14 extend in the transverse direction B from the respective side edges 11 of the rear waist region 7. Leg elastic members 16 extending in the back-and-forth direction A are interposed between the topsheet 8 and the backsheet 9 along the respective side edges 11 of the chassis 2 and secured in a stretched state to at least one of these sheets 8, 9. A waist elastic member 17 extending in the transverse direction B is interposed between the topsheet 8 and the backsheet 9 along the end 12 of the rear waist region 7 and bonded in a stretched state to at least one of these sheets 8, 9. The front and rear wings 13, 14 are made of a nonwoven fabric, a plastic film or a laminate thereof and the rear wings 14 are provided on respective inner surfaces with fasteners 18 formed from pressure-sensitive adhesives or the like. To put the diaper 1 on the wearer, the rear wings 14 may be detachably anchored on the backsheet 9 in the front waist region 6 at predetermined positions or on outer surfaces of the respective front wings 13.

The body fluid absorbent panel 3 comprises an upper sheet 21, a lower sheet 22 and an absorbent core 23 interposed between these two sheets 21, 22. The upper sheet 21 as well as the lower sheet 22 extend beyond a peripheral edge 24 of the core 23 and are overlapped and bonded together by means of adhesives or suitable welding technique outside the peripheral edge 24 to form a pair of side edges 26 extending in the back-and-forth direction A and a pair of ends 27 extending in the transverse direction B. In the vicinity of the respective side edges 26, leak-barrier cuffs 28 extending in the back-and-forth direction A are formed. The leak-barrier cuffs 28 respective comprise distal edges 31, proximal edges 32, front ends 33 and rear ends 34. The proximal edges 32, the front ends 33 and the rear ends 34 are bonded to the upper sheet 21 and/or the lower sheet 22 along the transversely opposite side edges 26 and the longitudinally opposite ends 27 of the body fluid absorbent panel 3 by means of adhesives 36. The distal edges 31 of the leak-barrier cuffs 28 are put aside from the proximal edges 32 toward a centerline C-C of the diaper 1 bisecting a width of the body fluid absorbent panel 3 and thereby partially cover the body fluid absorbent panel 3. Elastic members 38 are attached in a stretched state to the inner side of sleeves 37 formed by the respective distal edges 31. The diaper 1 of FIG. 1 constructed in this manner is adapted to bow inward as the leg elastic members 16, the waist elastic member 17 and the elastic members 38 operatively associated with the respective leak-barrier cuffs 28. Thereupon, the chassis 2 and the body fluid absorbent panel 3 are folded along first, second and third folding guide means 51, 52, 53 (See FIGS. 3 and 4) indicated by imaginary lines P-P, Q-Q and R-R extending in the crotch region 5 in the transverse direction to take a posture as shown in FIG. 2.

Figure 3:
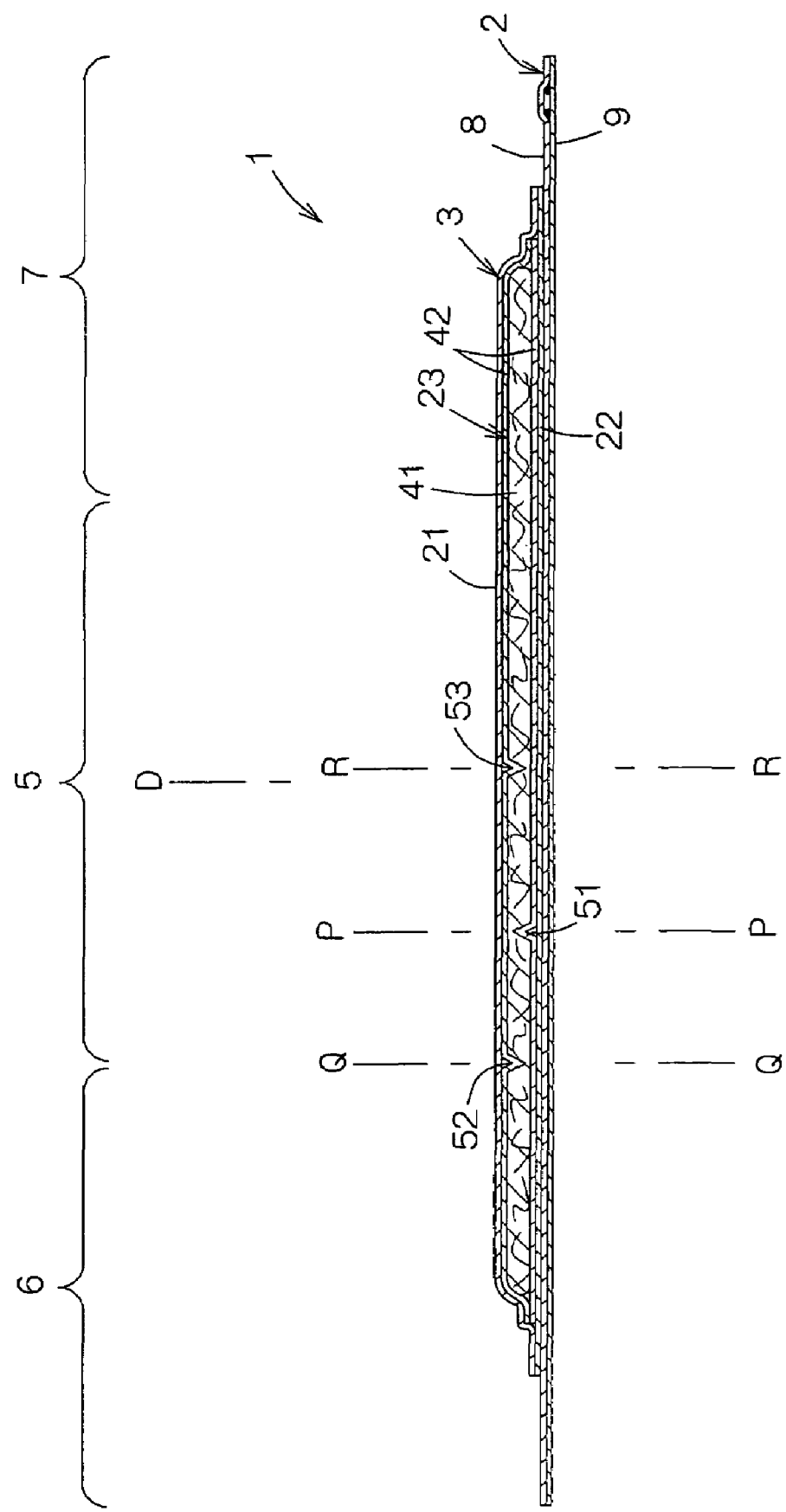
FIG. 3 is a sectional view taken along the line III-III in FIG. 1.
Figure 4:
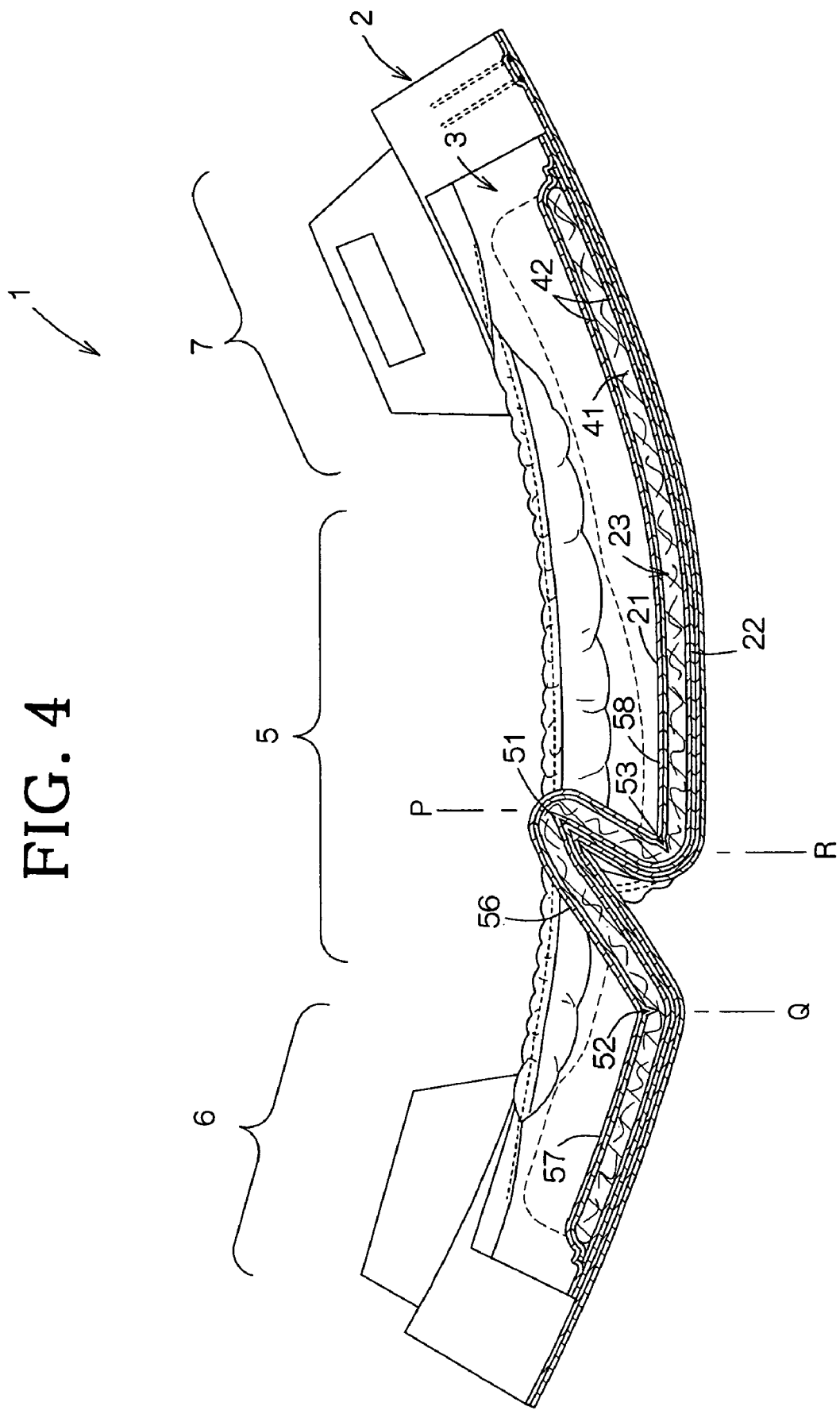
FIG. 4 is a sectional view taken along the line IV-IV in FIG. 2.

FIG. 3 is a sectional view taken along the line III-III in FIG. 1 and FIG. 4 is a sectional view taken along the line IV-IV in FIG. 2 wherein the line III-III coincides with the centerline C-C in FIG. 1 and the line IV-IV coincides with the centerline C-C in FIG. 2. The upper sheet 21 of the body fluid absorbent panel 3 is liquid-pervious and made of a nonwoven fabric or a perforated plastic film. The lower sheet 22 is liquid-impervious or liquid-pervious and made of a nonwoven fabric or a plastic film. The core 23 sandwiched between the upper sheet 21 and the lower sheet 22 comprises body fluid absorbent materials 41 such as fluff pulp fibers or a mixture of fluff pulp and super-absorbent polymer particles wrapped with a liquid-pervious sheet 42 having a high body fluid diffusibility such as a tissue paper. The core 23 is panel-like shaped and, more specifically, has a generally hourglass-like planar shape (See FIG. 1), i.e., in the crotch region 5, the transversely opposite side edges of the core 23 bow inward so that the width of the core 23 in this crotch region 5 is smaller than those in the front and rear waist regions 6, 7. The liquid-pervious sheet 42 is preferably bonded to both the upper sheet 21 and the lower sheet 22 by means of hot melt adhesives. This core 23 is formed on its surface facing the lower sheet 22 with the first folding guide means 51 in the form of a V-shaped groove extending along the imaginary line P-P (See FIG. 1) across the core 23 and on its surface facing the upper sheet 21 with the second and third folding guide means 52, 53 in the forms of V-shaped grooves extending along the imaginary lines Q-Q and R-R across the core 23. Preferably, the first folding guide means 51 is formed to be put aside toward the front waist region 6 from a centerline D-D bisecting a dimension of the diaper 1 as measured in the back-and-forth direction as illustrated in FIGS. 1 and 3. With the diaper 1 of FIG. 3 put on the wearer, the leg elastic members 16 as well as the elastic members 38 of the leak-barrier cuffs 28 contract and thereby reduce a dimension of the body fluid absorbent panel 3 as measured in the back-and-forth direction as the diaper 1 bows in the back-and-forth direction A. Under such an effect of these elastic members, the body fluid absorbent panel 3 is folded in the vicinity of the first folding guide means 51 so as to describe a generally inverted V-shaped cross-section inward so that a crest 56 protruding toward the wearer (not shown) are formed while the body fluid absorbent panel 3 is folded in the vicinity of the second and third folding guide means 52, 53 so as to describe generally V-shaped cross-sections so that troughs 57, 58 spaced from the diaper wearer are formed as will be seen in FIG. 4. The crest 56 of the diaper 1 shown in FIG. 4 functions to block a flow of urine moving from the front waist region 6 toward the rear waist region 7 and block a flow of loose passage from the rear waist region 7 toward the front waist region 6. In this way, this diaper 1 is free from an anxiety that the genital organ and the vicinity thereof as well as the crotch region 5 of the diaper wearer might be soiled with urine and loose passage commingling together.

In the illustrated diaper 1, the first, second and third folding guide means 51, 52, 53 are not limited to the V-shaped grooves but may be replaced by the grooves of the other shapes such as U-shape. Alternatively, the body fluid absorbent panel 3 may be provided with a plurality of stripe-like zones extending in parallel one to another across the body fluid absorbent panel 3 so that a stiffness of this body fluid absorbent panel 3 may be lower in each of these stripe-like zones than in the remaining zone and these stripe-like zones may function as the first, second and third folding guide means 51, 52, 53. In order that the body fluid absorbent panel 3 can be easily folded along the first, second and third folding guide means 51, 52, 53 to form the crest 56, it is preferred to adopt the core 23 of the generally hourglass-like planar shape as in the illustrated embodiment in which the core 23 has a width narrower in the crotch region 5 than in the front and rear waist regions 6, 7. It is also preferred to bond the body fluid absorbent panel 3 to the chassis 2 at a proportion of actually bonded area in the crotch region 5 lower than in the front and rear waist regions 6, 7. In this way, the body fluid absorbent panel 3 can be further easily folded along the first, second and third folding guide means 51, 52, 53. In addition, the chassis 2 and the body fluid absorbent panel 3 may be bonded together along a plurality of striped bonding zones extending in the transverse direction B to alleviate a possibility that a flexural rigidity of the body fluid absorbent panel 3 in the back-and-forth direction A might undesirably increase due to bonding these chassis 2 and body fluid absorbent panel 3 to each other.

In the illustrated diaper 1, the liquid-impervious plastic film used as the topsheet 8 of the chassis 2 may be replaced by a liquid-pervious film or a nonwoven fabric or even omitted so far as the lower sheet 22 of the body fluid absorbent panel 3 is liquid-impervious. The lower sheet 22 of the body fluid absorbent panel 3 may be replaced by a liquid-pervious plastic film or a nonwoven fabric so far as the topsheet 8 is made of a liquid-impervious plastic film.

According to this invention, in regions 61 indicated in FIGS. 1 and 2, the distal edges 31 of the respective leak-barrier cuffs 28 may be bonded to the upper sheet 21 of the body fluid absorbent panel 3 to facilitate the body fluid absorbent panel 3 to be folded along the first folding guide means 51 and thereby to facilitate the crest 56 to be formed. The regions 61 lie in the vicinity of the first folding guide means 51 and at least one of the second and third folding guide means 52, 53 may be omitted so far as the formation of the crest 56 is significantly facilitated by utilizing the regions 61 in this manner. While the proximal edges 32 of the respective leak-barrier cuffs 28 are illustrated to be bonded to the side edges 26 of the body fluid absorbent panel 3, respectively, it is possible without departing from the scope of this invention to bond the proximal edges 32 of the respective leak-barrier cuffs 28 to the chassis 2 in the vicinity of these side edges 26.

Figure 5:
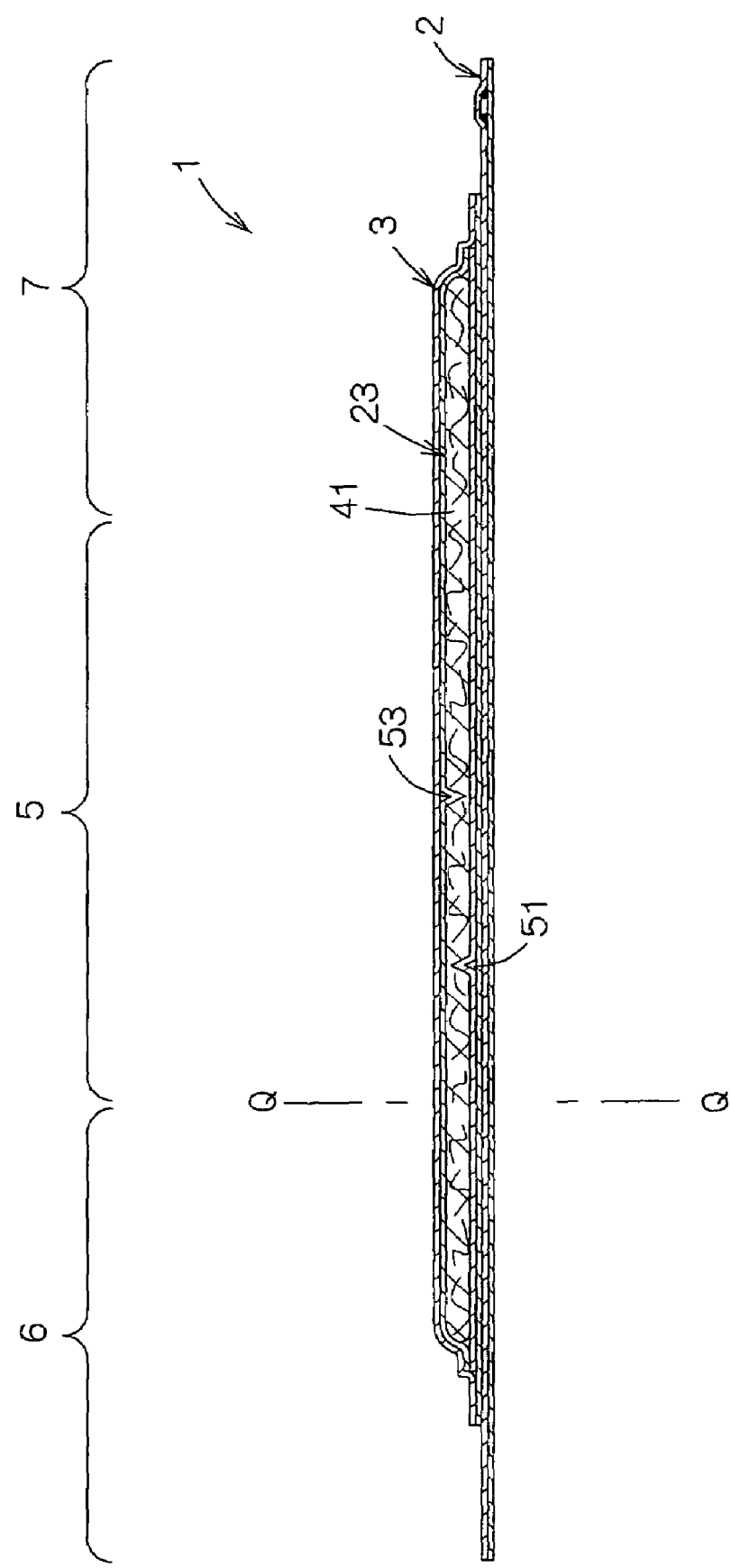
FIG. 5 is a view similar to FIG. 3, showing a second embodiment of the invention.
Figure 6:
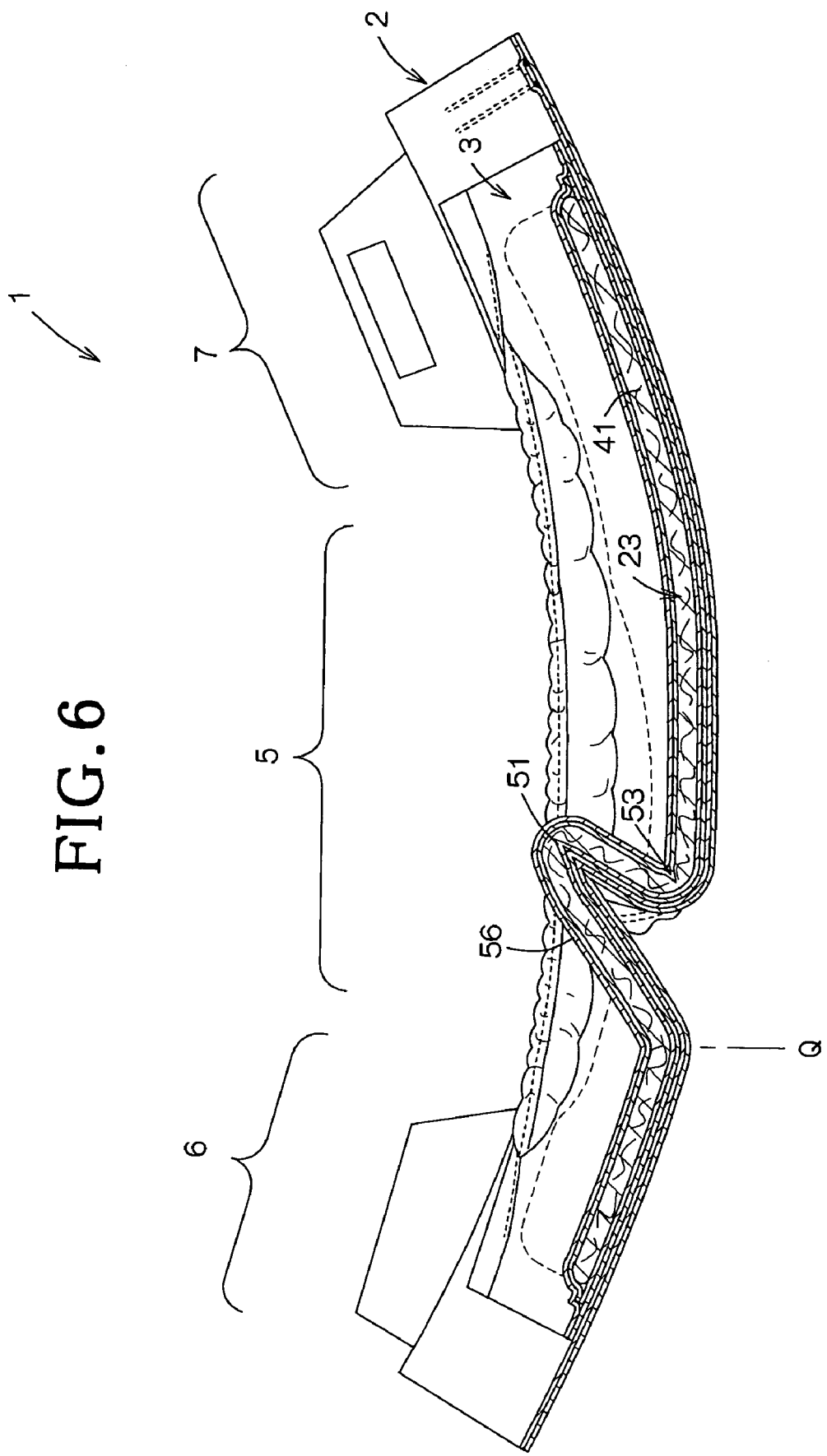
FIG. 6 is a sectional view taken along the line VI-VI in FIG. 5.

FIGS. 5 and 6 are views similar to FIGS. 3, 4, respectively, showing a second embodiment of the invention. The diaper 1 illustrated and described herein is similar to the diaper 1 of FIG. 1 in that the body fluid absorbent panel 3 includes the first folding guide means 51 and the third folding guide means 53 but distinguished from the diaper 1 of FIG. 1 in that the body fluid absorbent panel 3 is devoid of the second folding guide means 52. In the diaper 1 illustrated in FIGS. 5 and 6, the body fluid absorbent materials 41 constituting the core 23 in the crotch region 5 has a relatively low material density particularly in a section put aside toward the front waist region 6. When such body fluid absorbent panel 3 is folded along the first folding guide means 51 to describe a generally inverted V-shape, the body fluid absorbent panel 3 is easily folded in the vicinity of a region indicated by an imaginary line Q in FIGS. 5 and 6 and a crest similar to the crest 56 illustrated in FIG. 3 can be formed.

This invention facilitates the production of the diaper free from an anxiety that urine and loose passage might commingle together in the crotch region.

What is claimed is:

1. A disposable diaper having a back-and-forth direction and a transverse direction being orthogonal to said back-and-forth direction, said diaper comprising:
   a front waist region;
   a rear waist region;
   a crotch region extending between said front and rear waist regions;
   a body fluid absorbent panel provided in at least said crotch region and extending in said back-and-forth direction;
   leak-barrier cuffs lying in a vicinity of transversely opposite side edges of said body fluid absorbent panel, respectively, and extending in said back-and-forth direction, said leak-barrier cuffs respectively having proximal edges and distal edges, wherein
      said proximal edges are bonded to said body fluid absorbent panel in the vicinity of the respective side edges, and
      said distal edges are laid inside with respect to the respective proximal edges as viewed in said transverse direction and elastically stretchable and contractible in said back-and-forth direction so as to cover a part of said body fluid absorbent panel; and
   said body fluid absorbent panel in said crotch region being formed with
      a first folding guide extending across said body fluid absorbent panel in said transverse direction so that said body fluid absorbent panel is folded inward along said first folding guide to describe a generally inverted V-sectional shape, and
      a second folding guide along which said body fluid absorbent panel can be folded so as to describe a generally V-sectional shape, said second folding guide lying toward said rear waist region from said first folding guide and extending in parallel to said first folding guide.

2. The diaper as defined by claim 1, wherein said distal edges of said leak-baffler cuffs are bonded to said body fluid absorbent panel in a vicinity of said first folding guide.

3. The diaper as defined by claim 1, wherein said body fluid absorbent panel comprises
- a liquid-pervious upper sheet adapted to come in contact with a wearer,
- a liquid-impervious or liquid-pervious lower sheet, and
- a body fluid absorbent core interposed between said two sheets and having a lower side adjacent said lower sheet and an upper side adjacent said upper sheet; and
wherein
- said first folding guide is a generally inverted V-shaped groove extending from the lower side of said body fluid absorbent panel toward the upper side; and
- said second folding guide is a generally V-shaped grooves extending from the upper side of said body fluid absorbent panel toward the lower side.

4. A disposable diaper having a back-and-forth direction and a transverse direction being orthogonal to said back-and-forth direction, said diaper comprising:
- a front waist region;
- a rear waist region;
- a crotch region extending between said front and rear waist regions;
- a body fluid absorbent panel provided in at least said crotch region and extending in said back-and-forth direction;
- leak-barrier cuffs lying in a vicinity of transversely opposite side edges of said body fluid absorbent panel, respectively, and extending in said back-and-forth direction, said leak-barrier cuffs respectively having proximal edges and distal edges, wherein
  - said proximal edges are bonded to said body fluid absorbent panel in the vicinity of the respective side edges, and
  - said distal edges are laid inside with respect to the respective proximal edges as viewed in said transverse direction and elastically stretchable and contractible in said back-and-forth direction so as to cover a part of said body fluid absorbent panel; and
- said body fluid absorbent panel in said crotch region being formed with a first folding guide extending across said body fluid absorbent panel in said transverse direction so that said body fluid absorbent panel is folded inward along said first folding guide to describe a generally inverted V-sectional shape;
wherein said body fluid absorbent panel is formed with, in addition to said first folding guide, at least one of
- a second folding guide along which said body fluid absorbent panel can be folded so as to describe a generally V-sectional shape, said second folding guide lying toward said front waist region from said first folding guide and extending in parallel to said first folding guide; and
- a third folding guide along which said body fluid absorbent panel can be folded so as to describe a generally V-sectional shape, said third folding guide lying toward said rear waist region from said first folding guide and extending in parallel to said first folding guide.

5. The diaper as defined by claim 4, wherein said body fluid absorbent panel comprises
- a liquid-pervious upper sheet adapted to come in contact with a wearer,
- a liquid-impervious or liquid-pervious lower sheet, and
- a body fluid absorbent core interposed between said two sheets and having a lower side adjacent said lower sheet and an upper side adjacent said upper sheet; and
wherein
- said first folding guide is a generally inverted V-shaped groove extending from the lower side of said body fluid absorbent panel toward the upper side; and
- said second and third folding guides are generally V-shaped grooves extending from the upper side of said body fluid absorbent panel toward the lower side.

* * * * *